United States Patent
Ukawa et al.

(10) Patent No.: US 10,791,941 B2
(45) Date of Patent: Oct. 6, 2020

(54) APPARATUS AND METHOD FOR MEASURING VENOUS PRESSURE

(71) Applicant: NIHON KOHDEN CORPORATION, Shinjuku-ku, Tokyo (JP)

(72) Inventors: Teiji Ukawa, Tokyo (JP); Haruka Morimoto, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 276 days.

(21) Appl. No.: 15/746,209

(22) PCT Filed: Aug. 3, 2016

(86) PCT No.: PCT/JP2016/003586
§ 371 (c)(1),
(2) Date: Jan. 19, 2018

(87) PCT Pub. No.: WO2017/022245
PCT Pub. Date: Feb. 9, 2017

(65) Prior Publication Data
US 2018/0206744 A1    Jul. 26, 2018

(30) Foreign Application Priority Data

Aug. 6, 2015  (JP) ................. 2015-155570

(51) Int. Cl.
*A61B 5/021*    (2006.01)
*A61B 5/0225*   (2006.01)
(Continued)

(52) U.S. Cl.
CPC ........ *A61B 5/02116* (2013.01); *A61B 5/0225* (2013.01); *A61B 5/02141* (2013.01);
(Continued)

(58) Field of Classification Search
CPC .......... A61B 5/021–02116; A61B 5/022–0235
See application file for complete search history.

(56) References Cited

U.S. PATENT DOCUMENTS 4,927,264 A    5/1990  Shiga et al.
5,606,977 A *  3/1997  Ramsey, III ....... A61B 5/02225
                                               600/494
(Continued)

FOREIGN PATENT DOCUMENTS

GB    1 598 984 A    9/1981
JP    54-86990 A     7/1979
(Continued)

OTHER PUBLICATIONS

Search Report dated Oct. 21, 2016, issued by the International Searching Authority in counterpart International Patent Application No. PCT/JP2016/003586 (PCT/ISA/210).
(Continued)

*Primary Examiner* — Meredith Weare
(74) *Attorney, Agent, or Firm* — Sughrue Mion, PLLC (57) ABSTRACT

A venous pressure measurement apparatus includes a pressure controller configured to change a pressure applied from a cuff to a portion of a body where a vein and an artery exist and to which the cuff is attached, a pulse wave detector configured to detect pulse waves from a pressure the cuff receives from the portion of the body, and a venous pressure calculating section configured to calculate a venous pressure based on the applied pressure and the pulse waves detected by the pulse wave detector during a period in which the applied pressure is changed. The pressure controller is configured to execute a plurality of measurement steps, the applied pressure being increased or reduced from an initial value in each of the measurement steps.

17 Claims, 8 Drawing Sheets

(51) Int. Cl.
  *A61B 5/00* (2006.01)
  *A61B 17/135* (2006.01)
  *A61B 5/024* (2006.01)
  *A61B 17/00* (2006.01)

(52) U.S. Cl.
  CPC ......... *A61B 5/02422* (2013.01); *A61B 5/7203* (2013.01); *A61B 5/7246* (2013.01); *A61B 17/1355* (2013.01); *A61B 2017/00119* (2013.01)

(56) References Cited

U.S. PATENT DOCUMENTS

| | | |
|---|---|---|
| 5,649,536 A | 7/1997 | Ogura et al. |
| 5,836,888 A | 11/1998 | Ogura et al. |
| 6,045,510 A | 4/2000 | Ogura et al. |
| 6,413,224 B1 | 7/2002 | Ogura et al. |
| 6,432,061 B1 | 8/2002 | Nissilä et al. |
| 2002/0120199 A1 | 8/2002 | Ogura et al. |
| 2012/0253209 A1 | 10/2012 | Ukawa et al. |
| 2013/0165787 A1 | 6/2013 | Ukawa et al. |
| 2015/0245772 A1 | 9/2015 | Kawamoto et al. |
| 2015/0265166 A1 | 9/2015 | Tanaka |
| 2015/0359437 A1* | 12/2015 | Maltz ................... A61B 5/6828 600/481 |

FOREIGN PATENT DOCUMENTS

| | | |
|---|---|---|
| JP | 7-236616 A | 9/1995 |
| JP | 2010-279654 A | 12/2010 |
| JP | 2011-200574 A | 10/2011 |
| JP | 2012-205822 A | 10/2012 |
| JP | 2013-146539 A | 8/2013 |
| JP | 5694032 B2 | 4/2015 |
| JP | 2015-160082 A | 9/2015 |
| RU | 2 107 456 C1 | 3/1998 |
| WO | 2014/054788 A1 | 4/2014 |

OTHER PUBLICATIONS

Written Opinion dated Oct. 21, 2016, issued by the International Searching Authority in counterpart International Patent Application No. PCT/JP2016/003586 (PCT/ISA/237).
Communication dated Jul. 1, 2019, issued by the Japanese Patent Office in counterpart Japanese Application No. 2015-155570.
Communication dated Jan. 30, 2019, issued by the Japanese Patent Office in counterpart Japanese Application No. 2015-155570.

* cited by examiner

APPARATUS AND METHOD FOR MEASURING VENOUS PRESSURE

TECHNICAL FIELD

The presently disclosed subject matter relates to an apparatus and method for measuring a venous pressure.

BACKGROUND ART

A venous pressure near a right atrium, so-called a central venous pressure, indicates a cardiac preload, and is an important index for monitoring circulatory dynamics. The central venous pressure can be invasively measured by inserting a catheter into a region rear the right atrium. Recently, a venous pressure measurement apparatus that can measure the central venous pressure by non-invasive means has been developed to reduce a burden on a subject.

According to a first related art, a venous pressure measurement method includes temporarily congesting a vein and detecting a venous pressure from an image formed by a transmission of near infrared rays at the time when venous blood restarts to flow from the congested state (see, e.g., JP2010-279654A). With this method, however, because the venous pressure is measured at the time when the venous blood restarts to flow from the congested state, the venous pressure cannot be measured under a natural condition of a body of the subject. Moreover, equipments such as a near-infrared light emitter and a near-infrared sensor are necessary.

According to a second related art, a venous pressure measurement apparatus is configured to measure a venous pressure under a natural condition of a body of a subject (see, e.g., JP5694032B2). Specifically, the venous pressure measurement apparatus is configured to change a pressure applied from a cuff to a portion of the body where an artery exists and to which the cuff is attached, and to detect the venous pressure in accordance with the applied pressure and a change in pulse waves received from the portion. Therefore, the venous pressure measurement apparatus can measure the venous pressure under a natural body condition and with a simple configuration using the cuff.

In this venous pressure measurement apparatus, the applied pressure is incremented from a given value (e.g., 0 mmHg) in a stepwise manner (e.g., by 10 mmHg), and the venous pressure is calculated based on pulse waves measured in a given range (e.g., 0 mmHg to 50 mmHg). In other words, the venous pressure measurement apparatus calculates the venous pressure based on the pulse waves acquired while changing the applied pressure from the initial value by given increments.

In the second related art, however, there is a room for further improving an accuracy of venous pressure measurement. Following are examples in which an improvement of the accuracy may be made.

A change width of stepping-up or stepping-down of the pressure applied is typically about 5 mmHg. Therefore, the venous pressure measurement apparatus of the second related art can obtain pulse waves that correspond only to such a change width (e.g., 5 mmHg) of the pressure, and hence the accuracy of the calculated venous pressure may not be sufficiently high.

Further, signal components of pulse wave detection signals are very small. Thus, when noises are included in the pulse wave detection signals, the venous pressure calculated by the venous pressure measurement apparatus of the second related art may not be so accurate.

Moreover, in the venous pressure measurement apparatus of the second related art, calculation of a change of the venous pressure over time is not considered. Therefore, it is not easy to monitor a condition change of a subject.

SUMMARY

Illustrative aspects of the present invention provide an apparatus and method for non-invasively measuring a venous pressure with an improved accuracy.

According to an illustrative aspect of the present invention, a venous pressure measurement apparatus includes a pressure controller configured to change a pressure applied from a cuff to a portion of a body where a vein and an artery exist and to which the cuff is attached, a pulse wave detector configured to detect pulse waves from a pressure the cuff receives from the portion of the body, and a venous pressure calculating section configured to calculate a venous pressure based on the applied pressure and the pulse waves detected by the pulse wave detector during a period in which the applied pressure is changed. The pressure controller is configured to execute a plurality of measurement steps, the applied pressure being increased or reduced from an initial value in each of the measurement steps

DESCRIPTION OF EMBODIMENTS

Figure 1:
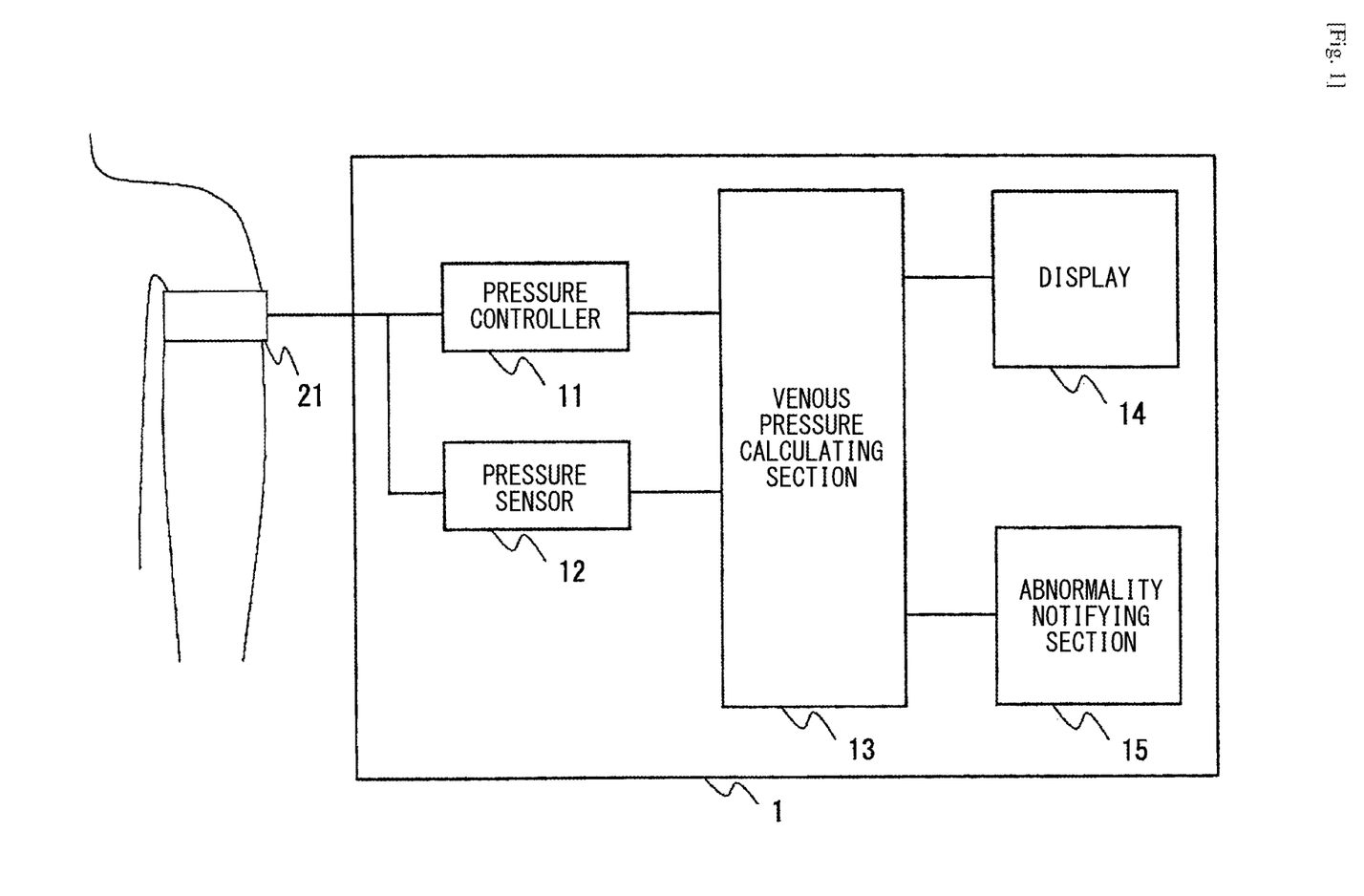
FIG. 1 is a block diagram illustrating a configuration of a venous pressure measurement apparatus according to an exemplary embodiment of the present invention.

Hereinafter, exemplary embodiments of the present invention will be described in detail with reference to the drawings. FIG. 1 is a block diagram illustrating a configuration of a venous pressure measurement apparatus 1 according to an exemplary embodiment of the present invention. The venous pressure measurement apparatus 1 includes a pressure controller 11, a pressure sensor 12, a venous pressure calculating section 13, a displaying section 14, and an abnormality notifying section 15. The venous pressure measurement apparatus 1 is adapted to be connected to a cuff 21 to be attached to a portion of a body of a subject.

The cuff 21 is wrapped around a portion of the body of the subject. Preferably, the portion of the body of the subject is an upper arm near the axillary cavity of the subject. In the following example, the cuff 21 is attached to the upper arm near the axillary cavity of the subject. The portion to which the cuff 21 is attached is not limited in so far as both the artery and the vein exist in the portion. The cuff 21 is, for example, an air bag configured to apply a pressure to the upper arm of the subject by an inflow of the air. In this case, the pressure applied by the cuff 21 is adjusted by the inflow amount of the air.

The pressure controller 11 is connected to the cuff 21. The pressure controller 11 adjusts the amount of the air flowing into the cuff 21. Therefore, the pressure controller 11 adjusts the pressure applied from the cuff 21 to the upper arm of the subject.

The pressure sensor 12 (an example of a pulse wave detector) is configured to detect a pulse wave which is vibration of a vessel wall occurring in the cuff 21. The pulse wave may include pulse waves of the artery and the vein. The pressure sensor 12 sends the detected pulse wave signal (pulse wave amplitude) of the venous pressure calculating section 13.

The pressure controller 11 executes a plurality of measurement steps in which the applied pressure is reduced in a stepwise manner (e.g., reduced by 5 mmHg at a time at given intervals) from the initial value (e.g., 50 mmHg). Alternatively, the pressure controller 11 may execute a plurality of measurement steps in which the applied pressure is increased in a stepwise manner (e.g., increased by 5 mmHg at a time at given intervals) from the initial value (e.g., 0 mmHg). The control of executing the plurality of measurement steps will be described in detail with reference to FIG. 2.

Figure 2:
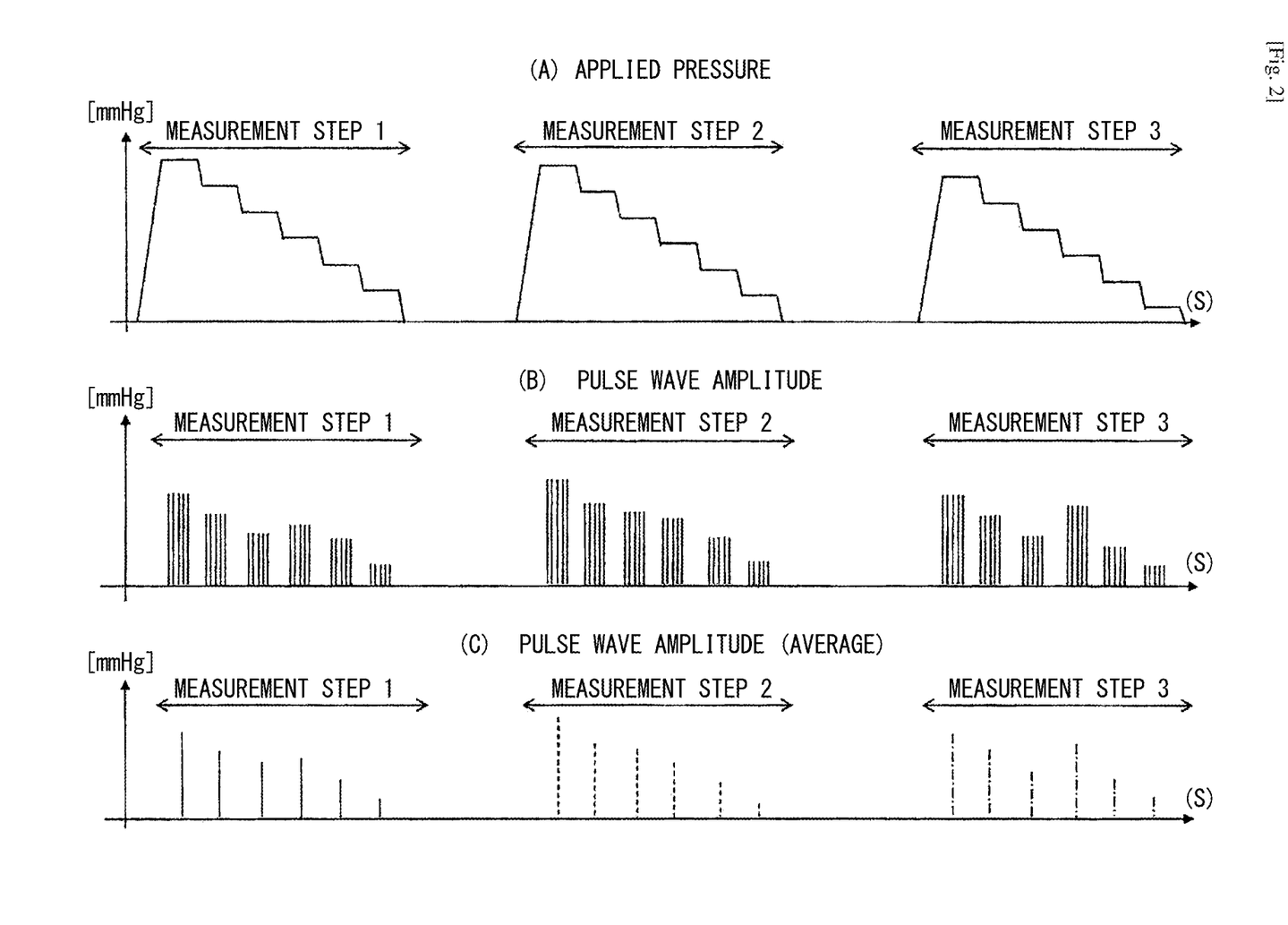
FIG. 2 is a set of charts illustrating operations of the venous pressure measurement apparatus.

FIG. 2 illustrates a plurality of measurement steps performed by the pressure controller 11. FIG. 2 includes (A) a chart illustrating a sequential change of the pressure applied by the cuff 21, (B) a chart illustrating a transition of the pulse wave amplitude (amplitude of the pulse wave) when the pressure applied by the cuff 21 is changed, and (C) a chart illustrating a transition (mean pulse wave amplitude at each applied pressure) of the pulse wave amplitude when the pressure applied by the cuff 21 is changed. In FIG. 2, the charts (A), (B) and (C) have a common time axis.

In the exemplary embodiment, the pressure controller 11 executes three measurement steps. Each measurement step includes a series of measurements in a period in which the applied pressure is changed in the reducing (or increasing) direction from the initial value. In the example of the chart (A) of FIG. 2, each of the Measurement Steps 1 to 3 includes a series of measurements in a period in which the applied pressure is reduced from the initial value to 0 in a stepwise manner. In a case in which the pressure is reduced from the initial value (a stepwise deflation) in the measurement step, the measurement step corresponds to a time period in which the applied pressure is changed from the initial value (e.g., a value equal to or higher than 40 mmHg) to a predetermined value (e.g., 2 mmHg, 0 mmHg in the example of the chart (A) of FIG. 2), i.e., the time period until the end of deflation. In a case in which the pressure is increased from the initial value (a stepwise inflation) in the measurement step, the measurement step corresponds to a time period in which the applied pressure is changed from the initial value (e.g., 0 mmHg) to a predetermined value (e.g., 40 mmHg), i.e., the time period until the end of inflation.

In each of the measurement steps in the exemplary embodiment, the initial value of the pressure applied by the cuff 21 is 40 to 50 mmHg (the chart (A) of FIG. 2). In each of the measurement steps, the pressure controller 11 reduces the applied pressure from the initial value in a stepwise manner by about 8 mmHg (a stepwise deflation). The pressure sensor 12 detects the amplitudes of the pulse waves when the pressure application is performed at respective applied pressures (the chart (B) of FIG. 2). In the example of the chart (A) of FIG. 2, at a timing when the applied pressure reaches 0 mmHg, the pressure controller 11 terminates each of the measurement steps. While deflation is performed in a stepwise manner by about 8 mmHg in the example of the chart (A) of FIG. 2, the decrements of the deflation may be, for example, about 5 mmHg each.

Preferably, the initial values (maximum values) of the applied pressure in the measurement steps are different values as described with reference to FIG. 3A. The pressure sensor 12 detects the average of the amplitudes of pulse waves which are detected during pressure applications at respective applied pressures (the chart (C) of FIG. 2). The pressure sensor 12 supplies information of the pulse wave amplitudes (the chart (C) of FIG. 2) and the applied pressures to the venous pressure calculating section 13.

Referring again to FIG. 1, the venous pressure calculating section 13 calculates the mean venous pressure in accordance with the pulse wave amplitudes which are measured in the measurement steps. A detailed example of the process will be described with reference to FIGS. 3A and 3B.

Figure 3A:
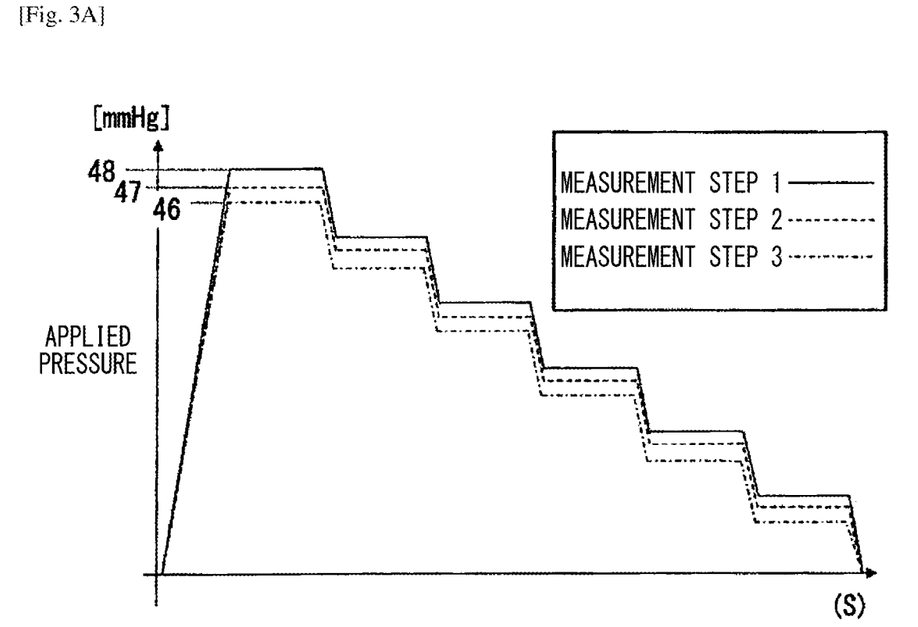
FIG. 3A is another chart illustrating the operations of the venous pressure measurement apparatus.

FIG. 3A is a view illustrating sequential changes of the applied pressures with respect to the pressure at the timing when each measurement step is started. As illustrated, preferably, the initial values of the applied pressures of the measurement steps are different from one another. In the measurement steps, preferably, the decrements (or the increments) of the applied pressures are substantially equal to each other. In the following example, the initial value of the applied pressure in Measurement Step 1 is 48 mmHg, the initial value of the applied pressure in Measurement Step 2 is 47 mmHg, and the initial value of the applied pressure in Measurement Step 3 is 46 mmHg. The decrements of the applied pressure is 8 mmHg each. The initial values and decrements (or increments) of the applied pressure may be different from this example.

Figure 3B:
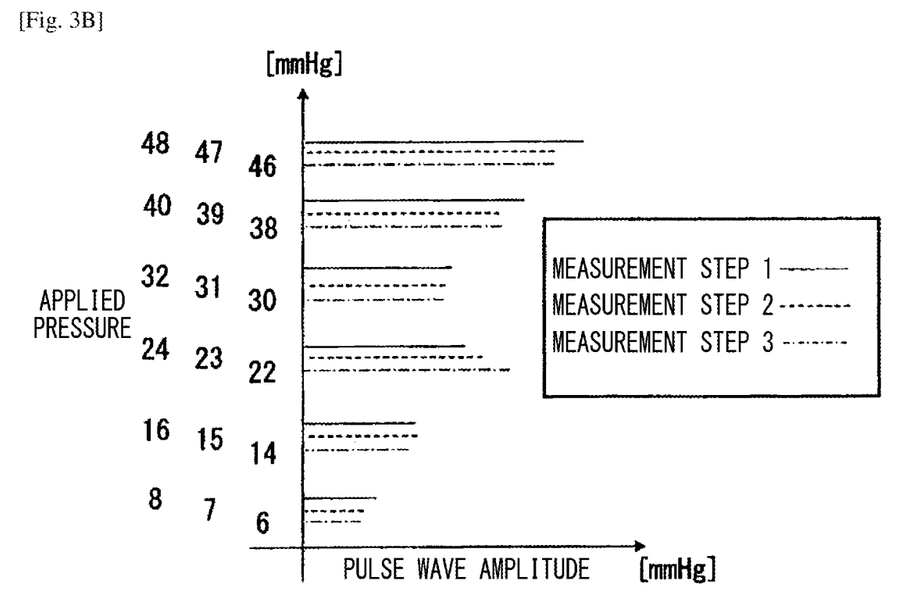
FIG. 3B is another chart illustrating the operations of the venous pressure measurement apparatus.

FIG. 3B is a graph showing relationships between the applied pressure and the pulse wave amplitude. The abscissa indicates the pulse wave amplitude, and the ordinate indicates the level of the applied pressure. In the example, the initial values of the applied pressures of the measurement steps are shifted from one another by 1 mmHg, and the decrements of the applied pressures are equal to one another (8 mmHg). Therefore, the applied pressures of the measurement steps are shifted from one another by 1 mmHg. Because the applied pressures of the measurement steps are shifted from one another by 1 mmHg shown in FIG. 3B, it is possible to finely break down the applied pressure. The venous pressure calculating section 13 calculates the venous pressure by using the relationships between the applied pressure and the pulse wave amplitude.

In each of the intervals between the measurement steps (the time period from the end of one of the measurement steps to the beginning of the next measurement step), it is preferable to dispose a time period in which the applied pressure is 0 (or a predetermined value which is near 0) (the chart (A) of FIG. 2). According to the configuration, the portion of the body of the subject returns to the normal condition, and congestion can be prevented from occurring in the next measurement step. Moreover, the disposition of the fixed time period in which the applied pressure is 0 leads to comply with the provision of the pressurization time period set forth in IEC 80601-2-30 (IEC 80601-2-30, Medical electrical equipment & #8211; Part 2-30: Particular requirements for the basic safety and essential performance of automated non-invasive sphygmomanometers).

Figure 4:
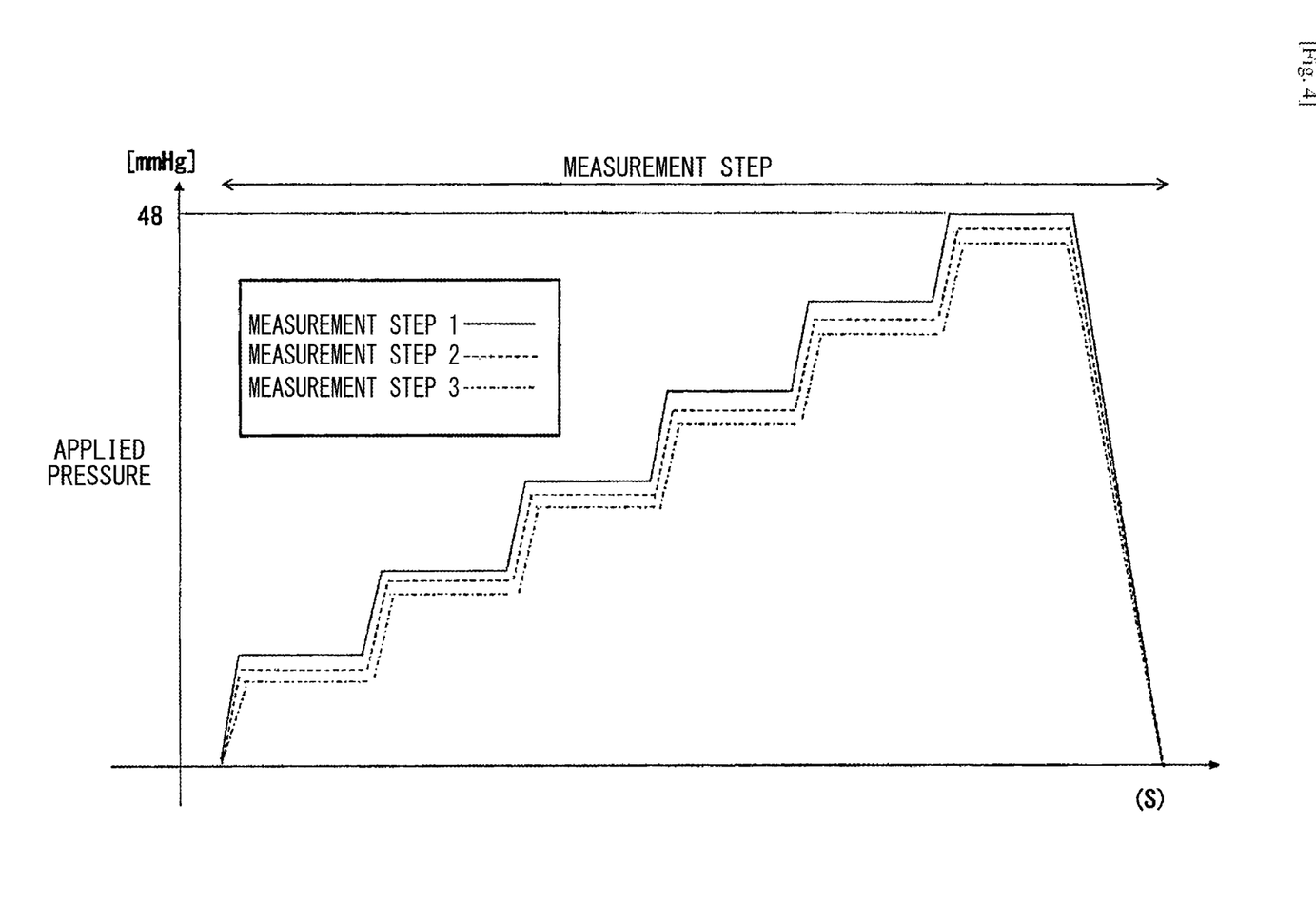
FIG. 4 is a diagram illustrating a control of applied pressure performed by a pressure controller of the venous pressure measurement apparatus.

While the applied pressure is reduced from the initial value in a stepwise manner in each measurement step in the examples shown in FIGS. 2, 3A and 3B, the pressure sensor 12 may set a small value (e.g., 0 mmHg) as the initial value of the applied pressure in each measurement step, and increase the applied pressure from this value. FIG. 4 is a diagram illustrating a control of applied pressure with the initial value of the applied pressure being a small value. In the example of FIG. 4, the applied pressure is finely divided by shifting only the initial increments of the measurement steps from one another by 1 mmHg. Alternatively, the initial values may be shifted from one another so as to be 0 mmHg, 1 mmHg, and 2 mmHg, respectively. Namely, it is preferable to shift the sequential change (a change of the value of the applied pressure due to elapse of time) of the applied pressure of a certain measurement step, from the sequential change (a change of the value of the applied pressure due to elapse of time) of the applied pressure of the subsequent (next) measurement step (FIGS. 3A and 4). The shifting of the sequential change of the applied pressure may be realized by shifting the initial values (FIG. 3A) or by setting the increments (or the decrements) of the applied pressure to have different values (FIG. 4). By shifting the sequential change of the applied pressure, it is possible to break down the applied pressure more finely.

The venous pressure calculating section 13 calculates the mean venous pressure from the relationships between the applied pressure and the pulse wave amplitude shown in FIG. 3B. The calculation method is substantially the same as the method disclosed in paragraphs 0070 to 0077 of JP5694032B2. An outline of the method will be briefly described. The venous pressure calculating section 13 presumes the applied pressure at the timing when the pulse wave amplitude detected by the cuff 21 is maximum, as the venous pressure (paragraph 0076 of JP5694032B2). In the above, the mean venous pressure is presumed by detecting an amplitude change of the pulse pressure which is caused by compression closing of the vein occurring when the applied pressure reaches the mean venous pressure (paragraph 0076 of JP5694032B2).

As described above, the venous pressure calculating section 13 calculates the venous pressure by using pulse wave amplitudes which are measured in a plurality of measurement steps. Namely, the venous pressure calculating section 13 performs one process of calculating the venous pressure by using measurement results of a plurality of measurement steps.

Referring again to FIG. 1, the displaying section 14 displays various calculation results (measurement values) calculated by the venous pressure calculating section 13, including the venous pressure, and waveforms. The displaying section 14 is a liquid crystal display disposed, for example, on the housing of the venous pressure measurement apparatus 1. Alternatively, the displaying section 14 may be a touch panel which receives an external signal for switching the display. The displaying section 14 may be detachable from the venous pressure measurement apparatus 1.

The abnormality notifying section 15 determines whether the venous pressure calculated by the venous pressure calculating section 13 exceeds a threshold or not. If the venous pressure exceeds the threshold, the section notifies this. This may be notified to the user by displaying an announcement that the measured venous pressure is abnormal, together with the measured venous pressure, or by transmitting the announcement that the measured venous pressure is abnormal, to another apparatus.

As illustrated in FIG. 3A, in two successive measurement steps, preferably, the initial values of the applied pressures are different from each other, and the decrements (or the increments) of the applied pressure are equal to each other. However, the exemplary embodiment is not limited to this. In all measurement steps, the initial values of the applied pressures may be exactly the same, and also the decrements (or the increments) of the applied pressure may be equal to each other. In this case, the sequential changes of the applied pressures in the measurement steps are identical to one another, and therefore only a plurality of pulse wave amplitudes of the applied pressures are supplied to the venous pressure calculating section 13. When three measurement steps in which the applied pressure is changed in the sequence of (48 mmHg, 40 mmHg, 32 mmHg, 24 mmHg, 16 mmHg, and 8 mmHg) are performed, for example, three pulse wave amplitudes at the applied pressure of 48 mmHg are supplied to the venous pressure calculating section 13. Similarly, also three pulse wave amplitudes at the applied pressure of 40 mmHg are supplied. The venous pressure calculating section 13 calculates the mean value of the three measurement values, and then calculates the venous pressure. Even in the case where noises enter the measurement value in a certain measurement step, therefore, influences of the noises are averaged. In the venous pressure measurement apparatus 1, consequently, the measurement accuracy can be improved as compared with the case only one measurement step is performed.

Advantages of the venous pressure measurement apparatus 1 of the exemplary embodiment will be described. As described above, the pressure controller 11 executes a plurality measurement steps, each including a series of measurements during an increase or decrease of the applied pressure from the initial value. The venous pressure calculating section 13 calculates the venous pressure based on pulse wave amplitudes obtained in the plurality of measurement steps. The number of samples of the pulse wave amplitude increases by performing a plurality of measurement steps, and therefore the venous pressure calculating section 13 can accurately detect the venous pressure.

When the initial value (first value) of the applied pressure in a certain measurement step is differentiated from the initial value (second value) of the applied pressure in the subsequent (in other word, next) measurement step, moreover, it is possible to break down the applied pressure more finely (FIG. 3A). By breaking down the applied pressure more finely, it is possible to improve the accuracy of the calculated venous pressure.

By shifting the initial values of applied pressures from one another and making the decrements (or the increments) of the applied pressure to be equal to each other (in the above-described example, 8 mmHg), the applied pressures of two successive measurement steps become completely different from each other. In FIGS. 3A and 3B, for example, the applied pressure in Measurement Step 1 is changed in the sequence of (48 mmHg, 40 mmHg, 32 mmHg, 24 mmHg, 16 mmHg, and 8 mmHg), that in Measurement Step 2 is changed in the sequence of (47 mmHg, 39 mmHg, 31 mmHg, 23 mmHg, 15 mmHg, and 7 mmHg), and that in Measurement Step 3 is changed in the sequence of (46 mmHg, 38 mmHg, 30 mmHg, 22 mmHg, 14 mmHg, and 6 mmHg). When, as described above, the initial values are shifted from one another, and decrements of the applied pressure are equalized, the applied pressures of two successive measurement steps are completely different from each other. This can break down the applied pressure more finely, and improve the accuracy of the calculated venous pressure. The effects are similarly attained also in the case where step pressurization is performed.

According to another exemplary embodiment of the present invention, a venous pressure measurement apparatus 1 is configured to, in addition to the operations of the exemplary embodiment described above, to remove pulse wave components on which noises are superimposed before calculating the venous pressure. Hereinafter, features of this exemplary embodiment that are different from those of the exemplary embodiment described above will mainly be described.

A configuration of the venous pressure measurement apparatus 1 of this exemplary embodiment is similar to the configuration illustrated in FIG. 1, and therefore its detailed description will be omitted. The pulse wave amplitude and the like in the case where noises are superimposed on the pulse wave will be described with reference to FIGS. 5 and 6.

Figure 5:
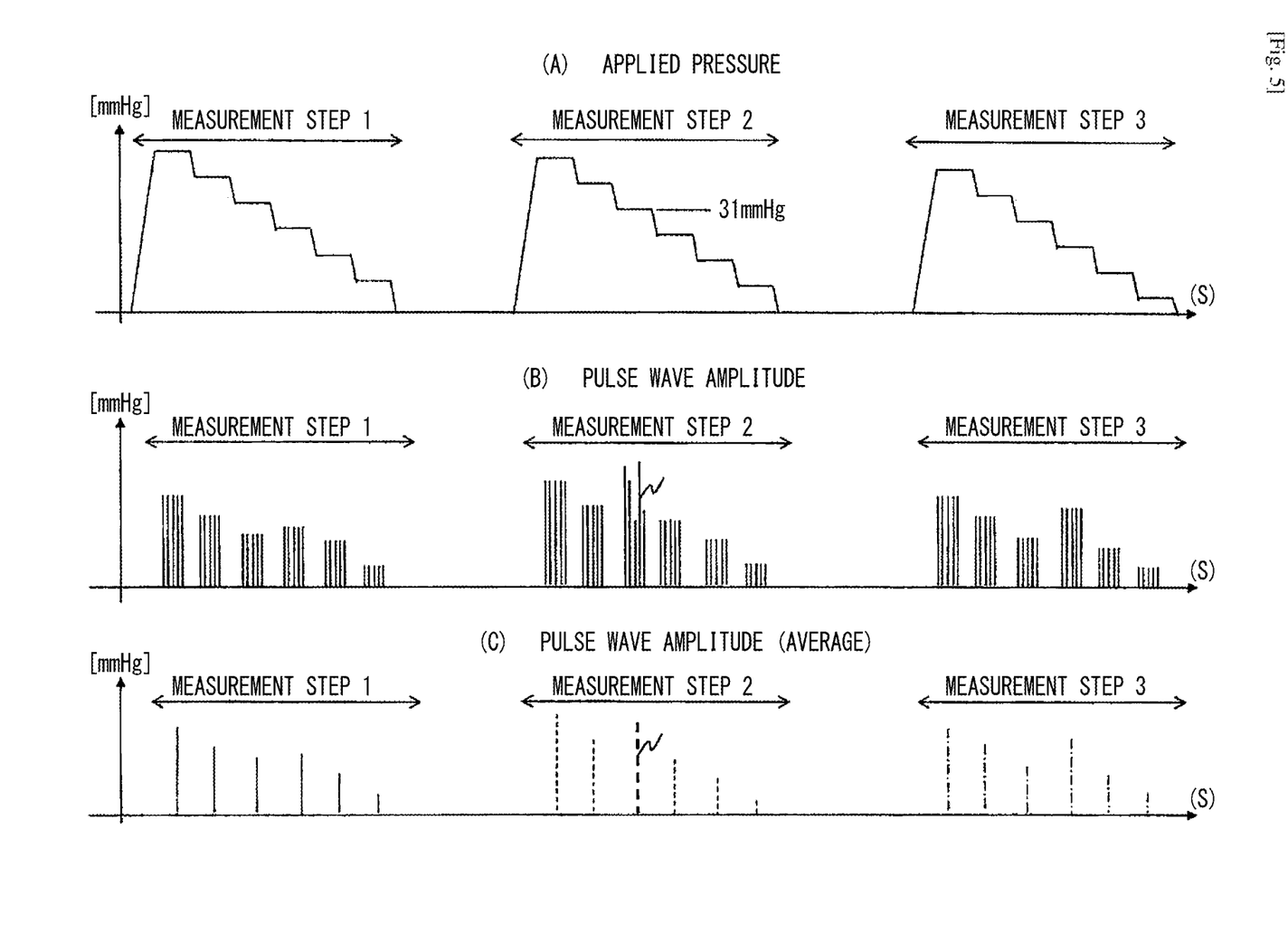
FIG. 5 is a set of charts illustrating operations of a venous pressure measurement apparatus according to another exemplary embodiment of the present invention.
Figure 6:
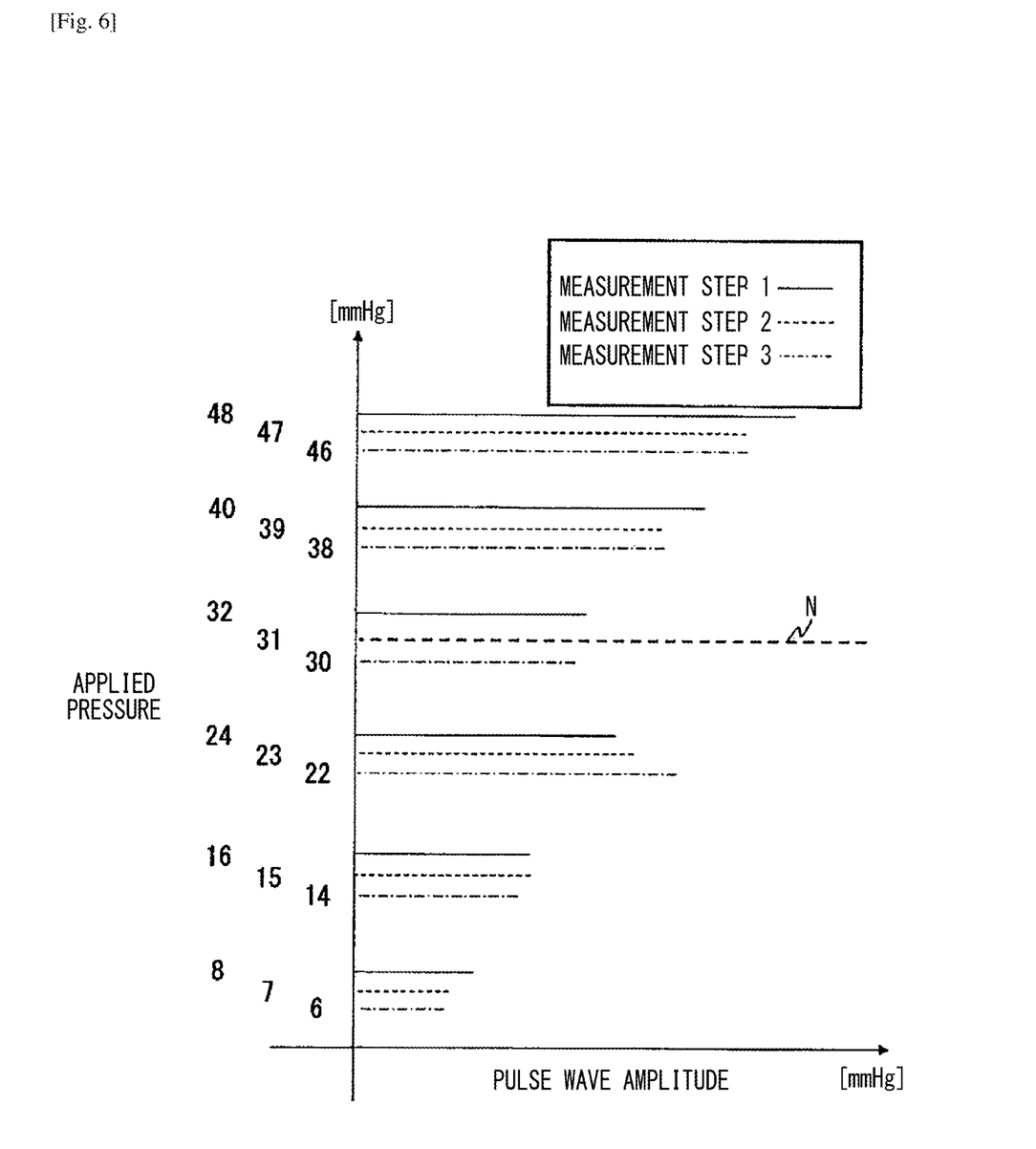
FIG. 6 is another chart illustrating the operations of the venous pressure measurement apparatus according to the exemplary embodiment of FIG. 5.

FIG. 5 includes (A) a chart illustrating a sequential change of the pressure applied by the cuff 21, (B) a chart illustrating a transition of the pulse wave amplitude when the pressure applied by the cuff 21 is changed, and (C) a chart illustrating a transition (mean pulse wave amplitude at each applied pressure) of the pulse wave amplitude when the pressure applied by the cuff 21 is changed. In FIG. 5, the charts (A), (B) and (C) have a common time axis. In the example shown in FIG. 5, the initial value of the applied pressure in Measurement Step 1 is 48 mmHg, the initial value of the applied pressure in Measurement Step 2 is 47 mmHg, and the initial value of the applied pressure in Measurement Step 3 is 46 mmHg. The decrements of the applied pressure is 8 mmHg each. FIG. 6 is a diagram illustrating relationships between the applied pressure and the pulse wave amplitude.

In the middle (31 mmHg) of the measurement of Measurement Step 2, noises are superimposed on the pulse wave amplitude ("N" in the chart (B) of FIG. 5). Namely, a value which is higher than the pulse wave amplitude derived from body of the subject is measured. Also in the case where the average of the pulse wave amplitude is calculated, a higher value which is affected by noises is calculated ("N" in the chart (C) of FIG. 5).

The pulse wave amplitude at the timing when the applied pressure is 31 mmHg is very higher than pulse wave amplitudes in the periphery (in the example, the timings when the applied pressure is 32 mmHg and 30 mmHg) ("N" in FIG. 6). The venous pressure calculating section 13 applies a statistical process on the relationships between the applied pressure and the pulse wave amplitude. For example, the venous pressure calculating section 13 sequentially compares the pulse wave amplitude at each applied pressure with the pulse wave amplitudes at adjacent applied pressures. Then, the venous pressure calculating section 13 detects outliers (i.e., pulse wave components on which noises are superimposed) from a result of the comparison process. The method of detecting outliers may be performed in accordance with a usual statistical analysis technique.

The venous pressure calculating section 13 eliminates the outliers (pulse wave components on which noises are superimposed), and then calculates the venous pressure in a similar manner as in the previously described exemplary embodiment. In the example of FIG. 6, the venous pressure calculating section 13 eliminates the pulse wave amplitude ("N" in FIG. 6) at the applied pressure of 31 mmHg, and then calculates the venous pressure. The method of calculating the venous pressure may be similar to the method of the exemplary embodiment described above and the method disclosed in JP5694032B2.

Then, effects of the venous pressure measurement apparatus 1 of the exemplary embodiment will be described. As described above, the venous pressure measurement apparatus 1 eliminates a pulse wave component on which noises are superimposed, and thereafter calculates the venous pressure. According to the configuration, influences of noises which enter during the measurement can be reduced, and therefore the venous pressure can be measured more accurately.

According to yet another exemplary embodiment of the present invention, a venous pressure measurement apparatus 1 is configured to measure the venous pressure in each measurement step, and to calculate the sequential change of the venous pressure by repeating the measurement step. Hereinafter, the venous pressure measurement apparatus 1 of this exemplary embodiment will be described with respect to features which are different from the exemplary embodiments described above.

A configuration of the venous pressure measurement apparatus 1 is similar to the configuration illustrated in FIG. 1, and therefore its detailed description will be omitted. Firstly, the operation of the venous pressure measurement apparatus 1 of the exemplary embodiment, and an example of variation of the pulse wave will be described with reference to FIG. 7.

Figure 7:
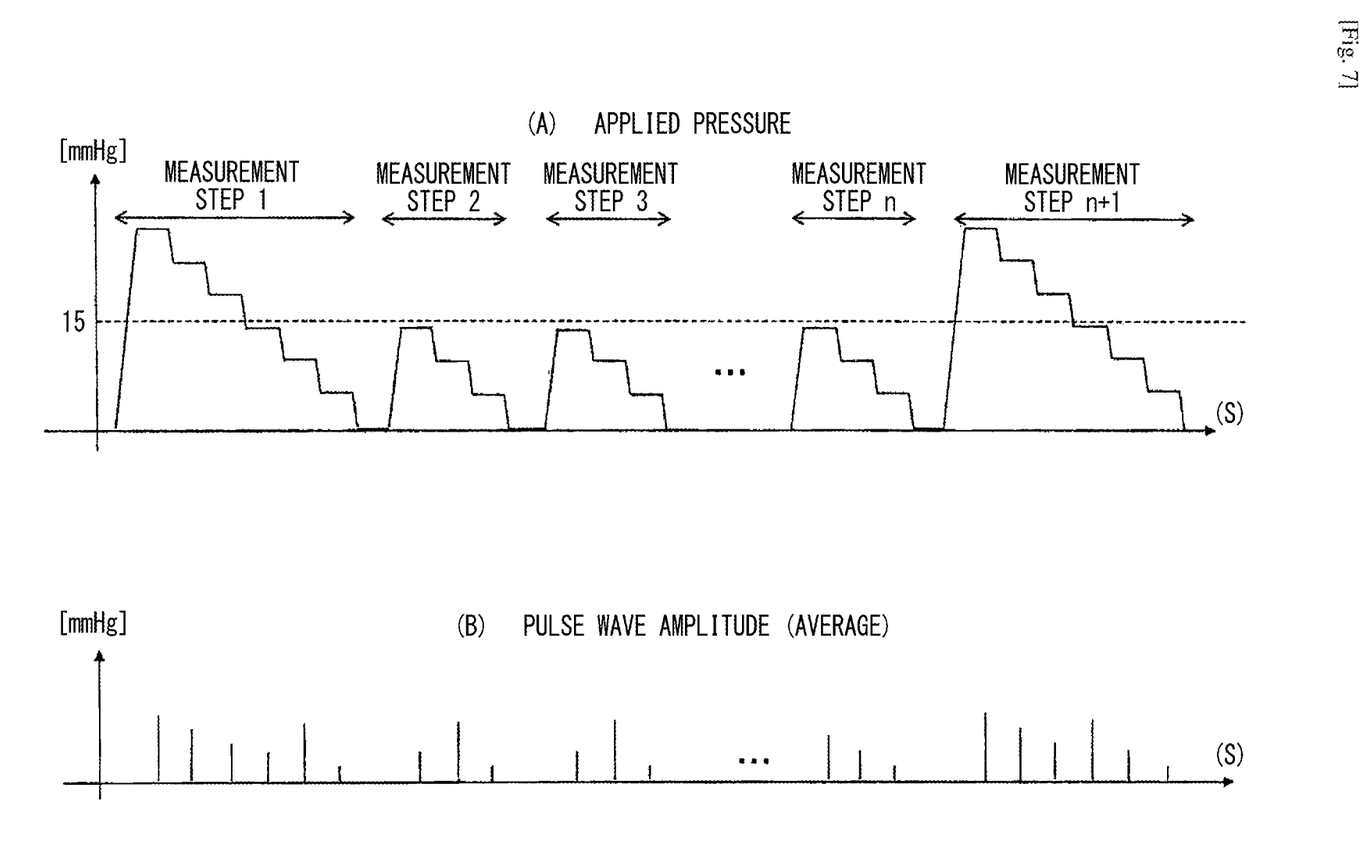
FIG. 7 is a set of charts illustrating operations of a venous pressure measurement apparatus according to another exemplary embodiment of the present invention.

FIG. 7 includes (A) a chart illustrating a sequential change of the pressure applied by the cuff 21, and (B) a chart illustrating a transition (mean pulse wave amplitude at each applied pressure) of the pulse wave amplitude when the pressure applied by the cuff 21 is changed. In order to simplify drawing, a chart illustrating a transition of the pulse wave amplitude when the pressure applied by the cuff 21 is changed (like the chart (B) of FIG. 5) is omitted, and only the mean pulse wave amplitude is illustrated in the chart (B) of FIG. 7.

In initial Measurement Step 1, in a manner similar to the previously described exemplary embodiment, the pressure controller 11 sets a sufficiently high value (e.g., 48 mmHg) as the initial value of the applied pressure, and then gradually reduces the applied pressure (a stepwise deflation). In a case in which the applied pressure is gradually increased (a stepwise inflation), the final applied pressure in Measurement Step 1 may have a sufficiently high value (e.g., 48 mmHg).

The venous pressure calculating section 13 calculates the venous pressure of the subject by using the pulse wave amplitudes which are measured in Measurement Step 1 (the chart (B) of FIG. 7). That is, the venous pressure calculating section 13 calculates the venous pressure of the subject by using only the pulse wave amplitudes which are measured in Measurement Step 1.

The pressure controller 11 determines whether the venous pressure calculated in Measurement Step 1 satisfies a condition indicative of a physiological abnormality of the body. Typically, the venous pressure of a subject is 10 mmHg or lower. Therefore, the pressure controller 11 determines, for example, whether the calculated venous pressure is equal to or lower than 15 mmHg.

If the venous pressure is within the normal range (equal to or lower than 15 mmHg), the pressure controller 11 executes Measurement Step 2 in which the maximum applied pressure is lower than a predetermined value (e.g., lower than 15 mmHg). In Measurement Step 2, for example, the pressure controller 11 changes the applied pressure to (14 mmHg, 9 mmHg, and 4 mmHg). The venous pressure calculating section 13 calculates the venous pressure of the subject by using the pulse wave amplitudes measured in Measurement Step 2 (the chart (B) of FIG. 7).

Among the measurement steps, a measurement step in which the applied pressure can be equal to or higher than the predetermined value is referred to as "high applied pressure measurement step," and a measurement step in which the applied pressure is lower than the predetermined value is referred to as "low applied pressure measurement step."

The pressure controller 11 determines whether the venous pressure calculated in Measurement Step 2 (low applied pressure measurement step) satisfies a condition indicative of a physiological abnormality of the body. Here, the condition indicative of a physiological abnormality of the body is preferably "the calculated venous pressure being equal to or higher than a predetermined value (e.g., 11 mmHg)." The condition is not limited to those in which a mere comparison with the predetermined value is performed, and, for example, may be those in which a temporal change of the venous pressure (e.g., the calculated values of the venous pressure have an increasing trend (e.g., an increasing trend continues three or more times)) or the like is considered.

If there is no physiological abnormality of the body, the pressure controller 11 continues Measurement Step 3 (low applied pressure measurement step).

In the example of FIG. 7, a physiological abnormality of the body is detected in Measurement Step n (n is an integer equal to or larger than 4) that is a low applied pressure measurement step. In this case, the pressure controller 11 executes a high applied pressure measurement step as Measurement Step n+1. That is, the pressure controller 11 shifts from the execution of a low applied pressure measurement step to the execution of a high applied pressure measurement step.

The venous pressure calculating section 13 calculates the venous pressure by using pulse wave amplitudes which are measured in Measurement Step n+1 that is a high applied pressure measurement step. The pressure controller 11 determines whether the venous pressure calculated in Measurement Step n+1 satisfies condition indicative of a physiological abnormality of the body. If a physiological abnormality of the body is detected, the pressure controller 11 continues a high applied pressure measurement step. If a physiological abnormality of the body is not detected, the pressure controller 11 shifts to a low applied pressure measurement step. The subsequent process is identical with the above described process.

The pressure controller 11 may control the measurement steps such that the high applied pressure measurement step is not executed consecutively for more than a predetermined number of times. This can reduce the burden on the body of the subject. In IEC 80601-2-30, a limitation related to an applied pressure which is applicable to the body of the subject is defined. For example, IFC 80601-2-30 defines that a pressure of 15 mmHg or higher should not be applied to the subject for 180 seconds or longer. Therefore, the pressure controller 11 may adequately switch over a high applied pressure measurement step and a low applied pressure measurement step so as to conform to such limitation.

The displaying section 14 displays calculated values of the venous pressure which are measured in the measurement steps.

Then, effects of the venous pressure measurement apparatus 1 of the exemplary embodiment will be described. In the exemplary embodiment, the venous pressure measurement apparatus 1 calculates the venous pressure of the subject in every measurement steps. Therefore, the doctor or the like can monitor the change of the venous pressure of the subject.

Moreover, the pressure controller 11 performs switching between a high applied pressure measurement step and a low applied pressure measurement step. Since a low applied pressure measurement step is performed, the burden on the body of the subject can be reduced.

Particularly, the pressure controller 11 determines whether there is a physiological abnormality of the body, based on the venous pressure, and switches over a high applied pressure measurement step and a low applied pressure measurement step in accordance with the determination. In the case where it is not necessary to accurately monitor the venous pressure (no physiological abnormality of the body), therefore, pressurization at a high level can be avoided, and hence the burden on the body of the subject can be reduced.

In the case where it is suggested that there is a physiological abnormality of the body, the pressure controller 11 performs a high applied pressure measurement step in which the venous pressure can be accurately calculated. In the case where there might be a physiological abnormality in the subject, therefore, the doctor or the like can correctly monitor the venous pressure.

While the present invention has been described with reference to certain exemplary embodiments thereof, the scope of the present invention is not limited to the exemplary embodiments described above, and it will be understood by those skilled in the art that various changes and modifications may be made therein without departing from the scope of the present invention as defined by the appended claims.

For example, the present invention is not limited to a stepwise changing of the applied pressure (i.e., stepwise deflation or stepwise inflation) like the exemplary embodiments described above. The pressure controller 11 may execute a control in which a measurement step of continuously (e.g., linearly) change the applied pressure from the initial value is performed a plurality of times.

In the exemplary embodiments described above, the cuff 21 is inflated for the purpose of detecting the venous pressure. However, the cuff 21 may be inflated to perform a regular blood pressure measurement simultaneously with the venous pressure measurement. In this case, in order to enable also the blood pressure to be measured, pressurization at a high level is performed in a certain measurement step (preferably, the first measurement step).

Although not illustrated, two cuffs may be attached to the subject as disclosed in JP5694032B2 (the first embodiment shown in FIG. 1 of JP5694032B2), thereby measuring the venous pressure. The method of attaching two cuffs to the subject, and calculating the venous pressure may be performed in a similar manner as the method disclose in JP5694032B2 (see, e.g., FIG. 2 of JP5694032B2).

Figure 8:
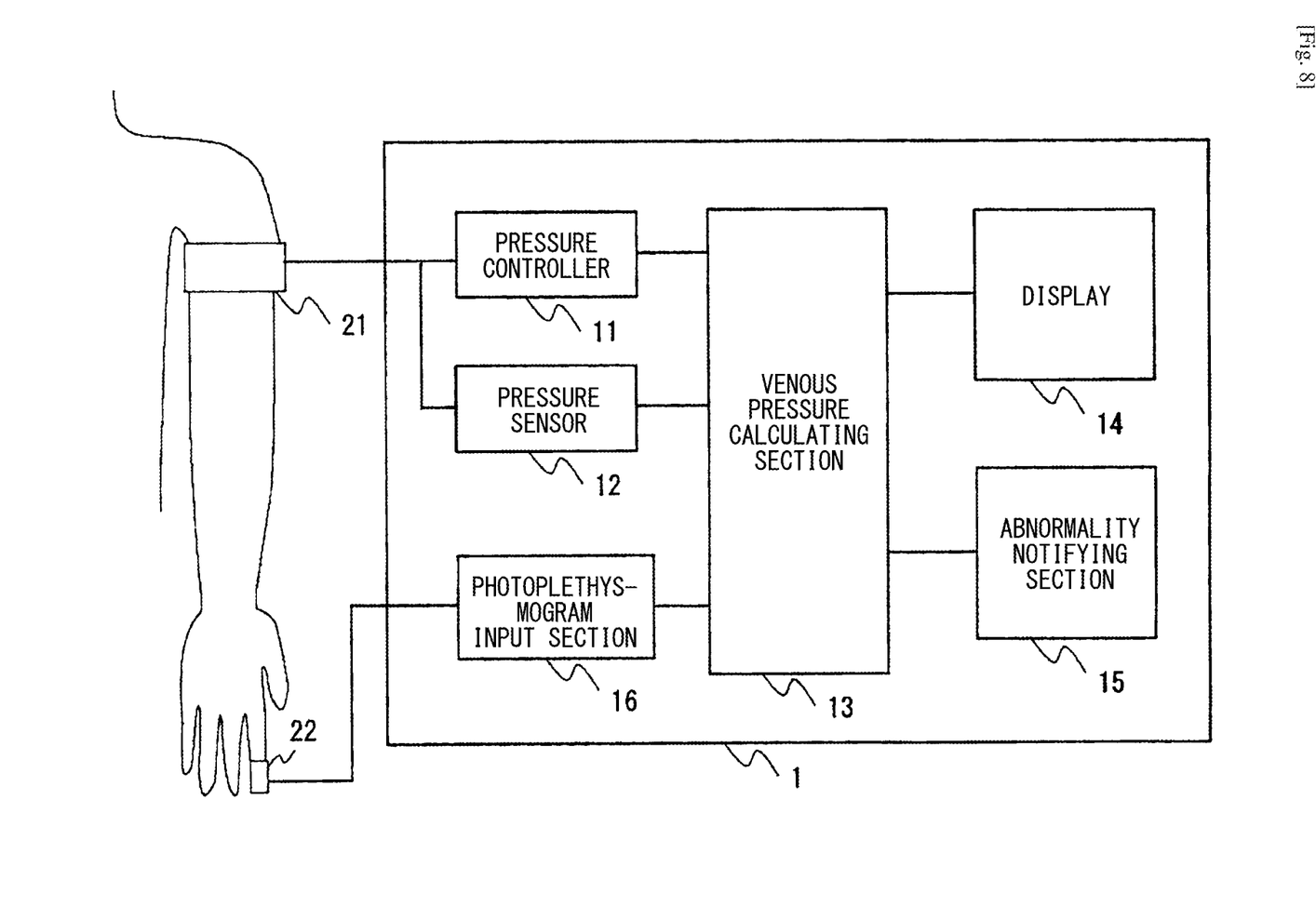
FIG. 8 is a block diagram illustrating a configuration of a venous pressure measurement apparatus according to another exemplary embodiment of the present invention.

The configuration of the apparatus is not limited to the one illustrated in FIG. 1. FIG. 8 illustrates another example of the venous pressure measurement apparatus 1.

The venous pressure measurement apparatus 1 illustrated in FIG. 8 has, in addition to the configuration of FIG. 1, a configuration in which a probe 22 is attachable (like the the fourth exemplary embodiment of JP5694032B2). For example, the probe 22 is a usual probe for measuring the arterial oxygen saturation (SpO2).

The probe 22 detects a photoplethysmogram which is referred in the calculation of the venous pressure. A photoplethysmogram input section 16 in the venous pressure measurement apparatus 1 supplies the photoplethysmogram which is acquired by the probe 22, to the venous pressure calculating section 13.

The venous pressure calculating section 13 calculates the venous pressure by using the pulse wave which is detected by the pressure sensor 12, and the photoplethysmogram which is acquired by the probe 22. The method of calculating the venous pressure may be similar to the method disclosed in paragraphs 0065 to 0068 of JP5694032B2. That is, the venous pressure calculating section 13 may calculate the venous pressure while the pulse wave which is detected by the pressure sensor 12 is treated as the first pulse wave discussed in JP5694032B2, and the photoplethysmogram which is acquired by the probe 22 is treated as the second pulse wave discussed in JP5694032B2.

Alternatively, the venous pressure calculating section 13 may calculate the venous pressure by using a reference pulse wave and the pulse waves which are detected by the pressure sensor 12. That is, the venous pressure calculating section 13 may calculate the venous pressure based on a correlation between the reference pulse wave and the pulse wave as disclosed in paragraphs 0079 to 0085 of JP5694032B2 (the sixth embodiment of JP5694032B2). Specifically, a pulse wave which is detected when the pressure applied by the cuff 21 is maximum is previously stored as the reference pulse wave. Thereafter, the pressure controller 11 changes the applied pressure as described above, and the pressure sensor 12 detects pulse waves in the measurement steps. The venous pressure calculating section 13 presumes the applied pressure at the timing when the correlation between the pulse wave (corresponding to the first pulse wave in JP5694032B2) detected by the pressure sensor 12 and the reference pulse wave is minimum, as the venous pressure. Regarding to the specific flow of the process, see JP5694032B2.

That is, the venous pressure may be calculating by using any one of the methods disclosed in JP5694032B2 (any one of the methods according to the first to sixth exemplary embodiments of JP5694032B2).

Finally, a summary of the venous pressure measurement apparatus 1 according to the foregoing exemplary embodiments will be described. In each of the venous pressure measurement apparatuses 1, as described above, a plurality of measurement steps are executed. In the case where the venous pressure is calculated one time by using pulse wave amplitudes measured in the plurality of measurement steps, it is possible to finely break down the applied pressure, and an accurate calculation result of the venous pressure can be obtained. In the case where the venous pressure is calculated in each of the measurement steps, a temporal change of the venous pressure can be monitored. That is, samples of the pulse wave amplitude are increased by performing a plurality of measurement steps. When the venous pressure measurement apparatuses 1 use many samples of the pulse wave amplitude, the venous pressure can be accurately calculated, or the changing situation of the venous pressure can be accurately calculated.

A part or the whole of the above-described processes of the pressure controller 11, the venous pressure calculating section 13, and the abnormality notifying section 15 may be realized as computer programs which are operated in the venous pressure measurement apparatus 1. That is, the venous pressure measurement apparatus 1 is an apparatus including a central processing unit (CPU) and a memory. The CPU reads programs in the memory, and executes the programs.

The programs may be stored in a non-transitory computer readable medium of any one of various types, and then supplied to the computer. The non-transitory computer readable medium includes tangible storage media of various types. Examples of the non-transitory computer readable medium are a magnetic recording medium (e.g., a flexible disk, a magnetic tape, and a hard disk drive), a magneto-optical recording medium (e.g., a magneto-optical disk), a CD-read only memory (CD-ROM), a CD-R, a CD-R/W, a semiconductor memory (e.g., a mask ROM, a programmable ROM (PROM), an erasable PROM (EPROM), a flash ROM, and a random access memory RAM)). Alternatively, the programs may be supplied to the computer by means of a transitory computer readable medium of any one of various types. Examples of the transitory computer readable medium include an electrical signal, an optical signal, and an electromagnetic wave. The transitory computer readable medium can supply the programs to the computer through a wired communication path such as a metal wire or an optical fiber, or a wireless communication path.

This application is based on Japanese Patent Application No. 2015-155570 filed on Aug. 6, 2015, the entire content of which is incorporated herein by reference.

The invention claimed is:

1. A venous pressure measurement apparatus comprising:
a pressure controller configured to change a pressure applied from a cuff to a portion of a body where a vein and an artery exist and to which the cuff is adapted to be attached;
a pulse wave detector configured to detect pulse waves from a pressure the cuff receives from the portion of the body; and
a venous pressure calculating section configured to calculate a venous pressure based on the applied pressure and the pulse waves detected by the pulse wave detector during a period in which the applied pressure is changed,
wherein the pressure controller is configured to execute a plurality of measurement steps, the applied pressure being increased or reduced from an initial value in each of the measurement steps, and
wherein a sequential change of the applied pressure in a measurement step of the plurality of measurement steps is shifted from a sequential change of the applied pressure in a subsequent measurement step of the plurality of measurement steps.

2. The venous pressure measurement apparatus according to claim 1, wherein the venous pressure calculating section is configured to statistically process the pulse waves obtained in each of the measurement steps, to detect a pulse wave component on which a noise is superimposed among the pulse waves, and to calculate the venous pressure after eliminating the detected pulse wave component.

3. The venous pressure measurement apparatus according to claim 2, wherein the venous pressure calculating section is configured to statistically process amplitudes of the pulse waves obtained in each of the measurement steps, to detect the pulse wave component on which the noise is superimposed among the amplitudes of the pulse waves, and to calculate the venous pressure after eliminating the detected pulse wave component.

4. The venous pressure measurement apparatus according to claim 1, wherein the pressure controller is configured to shift the sequential change of the applied pressure in the measurement step from the sequential change of the applied pressure in the subsequent step.

5. The venous pressure measurement apparatus according to claim 4, wherein the pressure controller is configured to set a first value as the initial value in said one of the measurement steps, and to set a second value, which is different from the first value, as the initial value in the subsequent one of the measurement steps.

6. The venous pressure measurement apparatus according to claim 1, wherein the pressure controller is configured to set increments or decrements of the applied pressure to be substantially equal to each other in each of the measurement steps.

7. The venous pressure measurement apparatus according to claim 1, wherein the venous pressure calculating section is configured to calculate the venous pressure for each of the measurement steps, based on amplitudes of the pulse waves obtained in each of the measurement steps.

8. The venous pressure measurement apparatus according to claim 7, wherein the measurement steps to be executed by the pressure controller includes a low applied pressure measurement step in which the applied pressure is lower than a predetermined value, and a high applied pressure measurement step in which the applied pressure is allowed to be equal to or higher than the predetermined value.

9. The venous pressure measurement apparatus according to claim 8, wherein the pressure controller is configured to shift from an execution of the high applied pressure measurement step to an execution of the low applied pressure measurement step, when the venous pressure calculated in the high applied pressure measurement step does not satisfy a condition indicative of a physiological abnormality of the body.

10. The venous pressure measurement apparatus according to claim 8, wherein the pressure controller is configured to shift from the execution of the low applied pressure measurement step to the execution of the high applied pressure measurement step, when the venous pressure calculated in the low applied pressure measurement step satisfies a condition indicative of a physiological abnormality of the body.

11. The venous pressure measurement apparatus according to claim 8, wherein the pressure controller is configured to control the high applied pressure measurement step such that the high applied pressure measurement step is not executed consecutively for more than a predetermined number of times.

12. The venous pressure measurement apparatus according to claim 1, wherein the pressure controller is configured to set the applied pressure to be equal to or lower than a predetermined value, during a period from an end of one of the measurement steps to a start of a subsequent one of the measurement steps.

13. The venous pressure measurement apparatus according to claim 1, further comprising an abnormality notifying section configured to provide a notification of abnormality when the venous pressure exceeds a threshold.

14. The venous pressure measurement apparatus according to claim 1, wherein the pressure controller is configured to inflate the cuff to perform a blood pressure measurement and the venous pressure measurement.

15. The venous pressure measurement apparatus according to claim 1, wherein the pressure controller is configured to change the applied pressure in a stepwise manner.

16. A venous pressure measurement method comprising:
changing a pressure applied from a cuff to a portion of a body where a vein and an artery exist and to which the cuff is attached;
detecting pulse waves from a pressure the cuff receives from the portion of the body; and
calculating a venous pressure based on the applied pressure and the pulse waves detected during a period in which the applied pressure is changed,
wherein changing the pressure comprises executing a plurality of measurement steps, the applied pressure being increased or reduced from an initial value in each of the measurement steps, and
wherein a sequential change of the applied pressure in a measurement step of the plurality of measurement steps is shifted from a sequential change of the applied pressure in a subsequent measurement step of the plurality of measurement steps.

17. A non-transitory computer readable medium storing a program that, when executed by a computer, causes the computer to execute a method comprising:
changing a pressure applied from a cuff to a portion of a body where a vein and an artery exist and to which the cuff is attached;
detecting pulse waves from a pressure the cuff receives from the portion of the body; and
calculating a venous pressure based on the applied pressure and the pulse waves detected during a period in which the applied pressure is changed,
wherein changing the pressure comprises executing a plurality of measurement steps, the applied pressure being increased or reduced from an initial value in each of the measurement steps, and
wherein a sequential change of the applied pressure in a measurement step of the plurality of measurement steps is shifted from a sequential change of the applied pressure in a subsequent measurement step of the plurality of measurement steps.

* * * * *